June 24, 1941. C. WESCHCKE Plant Pat. 476
APRICOT
Filed Aug. 16, 1940
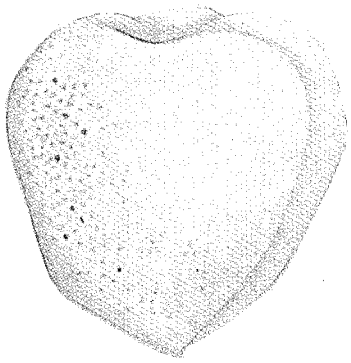
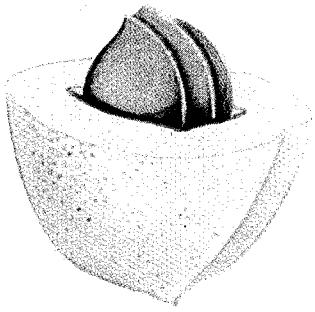
Inventor:
Carl Weschcke Patented June 24, 1941

Plant Pat. 476

UNITED STATES PATENT OFFICE

476

APRICOT

Carl Weschcke, St. Paul, Minn.

Application August 16, 1940, Serial No. 352,917

1 Claim. (Cl. 47—62)

My discovery relates to apricots. The object of the invention is to provide a new and hardy apricot variety with ornamental, edible, early-ripening fruit of high quality.

Reference being had to the accompanying colored drawing forming part thereof. The figure shows a full perspective view of the whole apricot in colors, below which is another view of the same apricot cut in half, showing the contrasting size of kernel in proportion to the edible flesh.

It has been grafted successfully on plum stocks and brought into fruiting at my nursery 5 miles east of River Falls, Wisconsin.

We have an affidavit on file from the United States Department of Agriculture Weather Bureau at River Falls, Wisconsin which certifies that on February 16, 1936, the minimum temperature at River Falls, Wisconsin was 47° below zero Fahrenheit, and that on January 24, 1936, the minimum temperature at River Falls was 40° below zero. This apricot had been grafted on plum stocks several years previous and successfully withstood these low temperatures without any signs of winter injury.

The figure shows irregularities in contour, different from those usually associated with an apricot, and the flecks of red against the background of deep apricot color help to further identify this fruit. The general texture and touch of the skin itself, however, is very similar to the average apricot.

The figure which shows the apricot-half, with the kernel intact, illustrates the free-stone nature of the pit which is extracted from the fruit usually so cleanly as to leave practically no adhering flesh.

The consensus of opinion from many who have eaten of this apricot is the same as to its high quality of taste and texture, the opinion being that it has a more pronounced apricot flavor than the average apricot which reaches St. Paul and Minneapolis markets.

This apricot fruit generally matures between the first and the fifteenth of August at River Falls, Wisconsin, when grafted on hybrid plum roots.

The variation in size is great. The original drawing shows an apricot slightly above average in size. Many of these apricots are larger. The pit or stone of the apricot is thicker than the average apricot stone although the length of the stone and general appearance is the same.

The fruit that has been stored in the ordinary mechanical refrigerator has kept wholesome for a week, none of the fruits so stored having begun to break down until some time during the second week of storage.

I claim:

The apricot variety herein disclosed, characterized by twigs having vigorous growth and resistance to sub-zero temperatures when grafted on plum stocks, and early-ripening fruit having irregular contour, skin with localized flecks of reddish purple against a background of rich apricot color, flesh with texture, flavor and keeping qualities as disclosed, and a thick stone.

CARL WESCHCKE.